(12) United States Patent
Yin et al.

(10) Patent No.: US 9,798,115 B1
(45) Date of Patent: Oct. 24, 2017

(54) COMPACT THREE-SURFACE WAFER-LEVEL LENS SYSTEMS

(71) Applicant: OmniVision Technologies, Inc., Santa Clara, CA (US)

(72) Inventors: Chuen-Yi Yin, New Taipei (TW); Jau-Jan Deng, Taipei (TW)

(73) Assignee: OmniVision Technologies, Inc., Santa Clara, CA (US)

( * ) Notice: Subject to any disclaimer, the term of this patent is extended or adjusted under 35 U.S.C. 154(b) by 0 days.

(21) Appl. No.: 15/138,510

(22) Filed: Apr. 26, 2016

(51) Int. Cl.
*G02B 3/00* (2006.01)
*G02B 9/04* (2006.01)
*G02B 13/00* (2006.01)
*G02B 9/10* (2006.01)
*G02B 23/24* (2006.01)

(52) U.S. Cl.
CPC .......... *G02B 13/0085* (2013.01); *G02B 3/00* (2013.01); *G02B 9/04* (2013.01); *G02B 9/10* (2013.01); *G02B 13/006* (2013.01); *G02B 23/243* (2013.01)

(58) Field of Classification Search
CPC ... G02B 9/04; G02B 9/06; G02B 9/08; G02B 9/10; G02B 13/0085

USPC .................................................. 359/784–795
See application file for complete search history.

(56) References Cited

U.S. PATENT DOCUMENTS

| | | | | |
|---|---|---|---|---|
| 2011/0249169 | A1* | 10/2011 | Hsu ..................... | G02B 13/0035 348/340 |
| 2011/0255856 | A1* | 10/2011 | Reshidko ............. | G02B 13/003 396/439 |
| 2014/0128673 | A1* | 5/2014 | Cheng ................... | G02B 13/06 600/109 |
| 2014/0334016 | A1* | 11/2014 | Yin ..................... | G02B 13/0085 359/714 |

* cited by examiner

*Primary Examiner* — Darryl J Collins
(74) *Attorney, Agent, or Firm* — Lathrop Gage LLP

(57) ABSTRACT

A compact three-surface wafer-level lens system for imaging a scene onto an image plane includes a one-sided wafer-level lens and a two-sided wafer-level lens disposed between the one-sided wafer-level lens and the image plane. The total track length of the wafer-level lens system is no more than 2.2 millimeters. The maximum transverse extent (in dimensions transverse to the optical axis) of the lens system and associated light propagating therethrough is no greater than 1.8 millimeters. The field of view angle of the lens system is at least 100 degrees.

18 Claims, 10 Drawing Sheets

COMPACT THREE-SURFACE WAFER-LEVEL LENS SYSTEMS

BACKGROUND

The demand for compact camera systems, and thus compact lens systems, delivering high performance is increasing with the growing use of imaging systems in a wide variety of applications. Such applications are found in areas such as consumer electronics, machine vision, automotive, and medical diagnostics and procedures.

Medical endoscopes used to examine an interior part of the human body constitute an example with challenging requirements to the size of the camera system. The camera system, including at least an image sensor, a lens system, and electronics, must fit within the area to be examined. Additionally, the camera system is often guided to the area of interest via passageways, such as an artery, which in itself imposes size constraints. Concurrently, high optical performance of the lens system of a medical endoscope camera system is desirable for achieving the goal of the procedure, for example an accurate diagnosis or a successful operation. However, the spatial requirements imposed by the use scenario limits the achievable performance of medical endoscope camera systems. Likewise, the size of endoscope cameras limits the use of medical endoscopes.

SUMMARY

Disclosed herein are compact lens systems suitable for employment in applications that are associated with tight spatial constraints and require good optical performance, for example medical endoscopes. These lens systems are manufactured at the wafer-level and may therefore be manufactured at a very low cost. These lens systems utilize the wafer-level process, and benefits uniquely associated therewith, to achieve good optical performance over a relatively large field of view in a compact package using three lens surfaces. Furthermore, these lens system may be formed using materials compatible with reflow soldering. This simplifies the manufacturing of camera modules that include the lens systems.

In an embodiment, a compact three-surface wafer-level lens system for imaging a scene onto an image plane includes a first wafer-level lens and a second wafer-level lens disposed between the first wafer-level lens and the image plane. The total track length of the wafer-level lens system is no more than 2.2 millimeters. The maximum transverse extent (in dimensions transverse to the optical axis) of the lens system and associated light propagating therethrough is no greater than 1.8 millimeters. The field of view angle of the lens system is at least 100 degrees. The first wafer-level lens includes (a) a first substrate having a first planar surface facing the scene and a second planar surface facing the image plane, wherein the distance from the first planar surface to the image plane defines the total track length, and (b) a first lens element formed on the second planar surface and having a first lens surface facing the image plane. The second wafer-level lens includes (a) a second substrate having a third planar surface facing the scene and a fourth planar surface facing the image plane, (b) a second lens element bonded to the third planar surface forming a second lens surface facing the scene, and (c) a third lens element bonded to the fourth planar surface forming a third lens surface facing the image plane.

In an embodiment, a compact three-surface wafer-level lens system for imaging a scene onto an image plane may include a first wafer-level lens and a second wafer-level lens disposed between the first wafer-level lens and the image plane. The lens system has effective focal length EFFL and total track length (TTL) such that $4.4<TTL/EFFL<5.4$. The first wafer-level lens includes (a) a first substrate having a first planar surface facing the scene and a second planar surface facing the image plane, wherein the distance from the first planar surface to the image plane defines the total track length (TTL) of the lens system, and (b) a first lens element formed on the second planar surface and having a first lens surface facing the image plane. The second wafer-level lens includes (a) a second substrate having a third planar surface facing the scene and a fourth planar surface facing the image plane, (b) a second lens element bonded to the third planar surface forming a second lens surface facing the scene, and (c) a third lens element bonded to the fourth planar surface forming a third lens surface facing the image plane.

In an embodiment, a compact three-surface wafer-level lens system for imaging a scene onto an image plane includes a first wafer-level lens and a second wafer-level lens disposed between the first wafer-level lens and the image plane. The first wafer-level lens includes (a) a first substrate having a first planar surface facing the scene and a second planar surface facing the image plane and (b) a first lens element formed on the second planar surface and having a concave lens surface facing the image plane, wherein the concave lens surface has diameter D1 and sag height SAG1 such that $3.2<D1/SAG1<4.2$. The second wafer-level lens includes a first convex lens surface facing the scene, and a second convex lens surface facing the image plane.

DETAILED DESCRIPTION OF THE EMBODIMENTS

Figure 1:
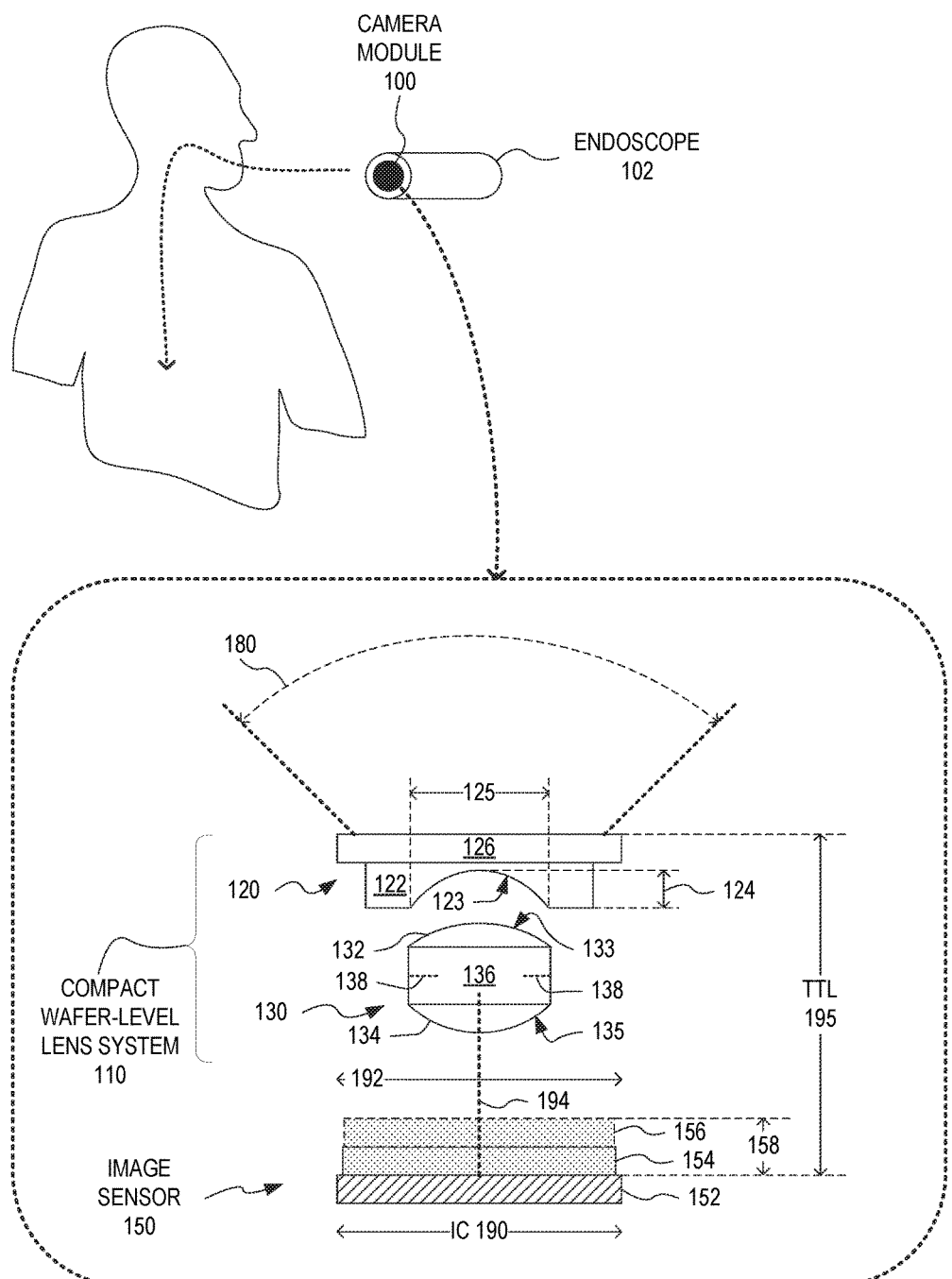
FIG. 1 illustrates a compact three-surface wafer-level lens system implemented in an exemplary camera device, according to an embodiment.

FIG. 1 illustrates one exemplary compact, three-surface wafer-level lens system 110 implemented in one exemplary camera module 100. Camera module 100 is, for example, configured for implementation in an endoscope 102, or in another device subject to tight spatial constraints. However, camera module 100 may be another type camera module without departing from the scope hereof. For example, camera module 100 may be a smartphone camera. Compact lens system 110 is coupled with an image sensor 150 in camera module 100.

Compact lens system 110 includes three lens surfaces 123, 133, and 135 that cooperate to achieve high quality imaging of a relatively wide field of view (FOV) in a compact package. Herein, a "lens surface" refers to a curved surface. In one embodiment, compact lens system 110 includes only these three lens surfaces, wherein lens surfaces 123 and 133 are separated by an air gap and lens surfaces 133 and 135 are separated by a solid portion. Compact lens system 110 may include one or more very slightly curved surfaces in addition to those shown in FIG. 1, without departing from the scope hereof. In one such example, a surface shown in FIG. 1 as being planar has a slight curvature.

Compact lens system 110 includes a one-sided wafer-level lens 120 and a two-sided wafer-level lens 130 optically coupled in series. Wafer-level lens 130 is disposed between wafer-level lens 120 and the image plane of compact lens system 110. One-sided wafer-level lens 120 includes a substrate 126 and a lens element 122 disposed on one surface of substrate 126. Lens element 122 is on the side of substrate 126 facing the image plane of compact lens system 110. Lens element 122 includes a lens surface 123 facing the image plane of compact lens system 110. In FIG. 1, the image plane of compact lens system 110 coincides with image sensor 150. Two-sided wafer-level lens 130 includes a substrate 136 and two lens elements 132 and 134 disposed on opposite facing surfaces of substrate 136. Lens element 132 is on a surface of substrate 136 facing away from the image plane of compact lens system 110. Lens element 134 is on a surface of substrate 136 facing the image plane of compact lens system 110. Lens element 132 includes a lens surface 133 facing away from the image plane of compact lens system 110, and lens element 134 includes a lens surface 135 facing the image plane of compact lens system 110.

The design of compact lens system 110 allows for wide FOV imaging in a compact package. Compact lens system 110 has a total track length (TTL) 195 and a maximum transverse extent 192. TTL 195 is the distance from the image plane of compact lens system 110 to the surface of compact lens system 110 closest to the scene and furthest away from the image plane, i.e., the surface of substrate 126 most distal from the image plane of compact lens system 110. In FIG. 1, the image plane of compact lens system 110 coincides with the light-receiving surface of an active layer 152 of image sensor 150. Maximum transverse extent 192 is the maximum extent of compact lens system 110, and associated light propagation through compact lens system 110 along TTL 195, in the dimensions orthogonal to the optical axis 194 of compact lens system 110. Thus, maximum transverse extent 192 is the maximum transverse extent of (a) wafer-level lenses 120 and 130 and (b) the image circle (IC) of compact lens system 110. In FIG. 1, the image circle of compact lens system 110 is represented by the diameter 190 of the image circle (IC).

In one embodiment, TTL 195 is 2.2 millimeters (mm) or less, and maximum transverse extent 192 is 1.8 mm or less. This embodiment of compact lens system 110 is well-suited for implementation in a camera module 100 of an endoscope 102.

Herein, the "image circle" of a lens system refers to a collection or set of the farthest positions, with respect to the position of the optical axis, that the cone of light transmitted by the lens system can reach on the image plane. For axially symmetric lens systems such as those disclosed herein, this collection or set describes a circle on the image plane. The image circle is defined herein as the circle that coincides with full width at half maximum of the cone at the image plane.

Herein, when referring to the diameter of an element of compact lens system 110 of image sensor 150, it is understood that this element may be of a rectangular shape (for example square) that encompasses the diameter. In one example, maximum transverse extent 192 is defined by an embodiment of substrate 126 having a diameter of about 1.1 mm. However, in this example, wafer-level lens 120 is manufactured to be square such that maximum transverse extent 192 is 1.1 mm times $\sqrt{2}$.

Compact lens system 110 has a relatively wide FOV characterized by a FOV angle 180. In certain embodiment, FOV angle 180 is at least 100 degrees, for example about 110 degrees. In one such embodiment, compact lens system 110 achieves this FOV angle 180 while TTL 195 is no more than 2.2 mm and maximum transverse extent 192 is no more than 1.8 mm.

In one embodiment, each of wafer-level lens 120 and wafer-level lens 130 has diameter similar to IC diameter 190. This is in stark contrast to the design conventionally used for lens systems having a relatively wide FOV, wherein the lens closest to the scene has a diameter that significantly exceeds the image circle diameter. In addition, TTL 195 of compact lens system 110 may be comparable to IC diameter 190 or at least only about 25% greater than IC diameter 190. For at least these reasons, compact lens system 110 may be combined with image sensor 150 in a camera module 100 that is significantly smaller than the package required when using a conventional lens system designed to achieve a relatively wide FOV.

Wafer-level lenses 120 and 130 are manufacturable at the wafer-level and compact lens system 110 may therefore be manufactured at low cost and in high volume. The wafer-level manufacturing method benefits from the compact transverse dimensions of wafer level lenses 120 and 130 to produce a very large number of wafer-level lenses per wafer. This gain in production yield is greater than the size-attributable gain achievable when using casting or machining to manufacture lenses In an embodiment, compact lens system 110 includes no other lenses that wafer-level lenses 120 and 130 and includes no other lens surfaces than lens surfaces 123, 133, and 135, which further simplifies the manufacturing process as compared to conventional lens systems having more lens elements and lens surfaces/interfaces.

Wafer-level lenses 120 and 130 benefit from wafer-level mass-production methods to enable lower manufacturing cost than those associated with cast lenses, such as molded glass lenses, or machined lenses. Furthermore, wafer-level production of wafer-level lens 130 allows for lens elements 132 and 134 to be made from a different material than that of substrate 136, as well as for lens elements 132 and 134 to be made from two different materials, respectively. Likewise, wafer-level production of wafer-level lens 120 allows for lens element 122 to be made from a different material than that of substrate 126. Such additional freedom of material choices, as compared to a cast or machined lens, provides additional flexibility to achieve desired performance characteristics of wafer-level lenses 120 and 130. In an embodiment, (a) lens element 122 is made of a different material than the material of substrate 126, (b) lens elements 132 and 134 are made from different materials than the material of substrate 136, and/or (c) lens elements 132 and 134 are made from two different materials, respectively.

Each of lens elements 122, 132, and 134 is integrally formed, that is, formed from one material and in one piece. Hence, each of lens elements 122, 132, and 134 is composed of a single material throughout. However, one or more of lens elements 122, 132, and 134 may include one or more surface coatings, such as an antireflective coating, without departing from the scope hereof.

In certain embodiments, camera module 100 is manufactured using reflow soldering to form at least some of the electrical contacts associated with image sensor 150 and an electronic circuit board (not shown in FIG. 1). For example, electrical contacts between image sensor 150 and the electronic circuit board are formed using reflow soldering after assembling compact lens system 110 with image sensor 150. It is advantageous to assemble compact lens system 110 with image sensor 150 prior to assembling image sensor 150 with the electronic circuit board. Not only may this order of assembly simplify the alignment of compact lens system 110 with image sensor 150, optical modules including compact lens system 110 and image sensor 150 may be mass-produced and subsequently incorporated in a variety of camera modules having different properties of the electronic circuit board.

In reflow soldering of an assembly, permanent electrical connections are formed by heating the assembly to melt solder paste disposed at contact interfaces of the assembly. Typically, the assembly is heated to about 250 degrees Celsius for about 10 seconds to form the permanent electrical connections. Therefore, in some embodiments of wafer-level lenses 120 and 130 are composed of materials that are compatible with reflow soldering; each of lens elements 122, 132, and 134 and each of substrates 126 and 136 is composed of a material that has identical, or substantially identical, optical properties before and after being subjected to a reflow soldering process. For example, each of lens elements 122, 132, and 134 and each of substrates 126 and 136 is composed of a material that has identical, or substantially identical, optical properties before and after being subjected to 260 degrees Celsius for 10 seconds.

In an embodiment, each of substrates 126 and 136 is substantially planar such that lens element 122 is disposed on a substantially planar surface of substrate 126, the surface of substrate 126 facing away from lens element 122 is substantially planar, and each of lens elements 132 and 134 is disposed on a substantially planar surface of substrate 136.

In an embodiment, substrate 136 includes a aperture stop 138 located between lens elements 132 and 134. Aperture stop 138 is for example an opaque coating. Aperture stop 138 may serve to maintain, at least to a certain degree, the symmetry of each ray bundle respectively associated with a field location, such that the angular spread of a ray bundle before wafer-level lens 130 is similar to the angular spread of the corresponding ray bundle after wafer-level lens 130.

Lens surface 123 is predominantly concave, while each of lens surfaces 133 and 135 is predominantly convex. However, the exact shapes of lens surfaces 123, 133, and 135 may be different from those shown in FIG. 1 without departing from the scope hereof. For example, each of lens surfaces 123, 133, and 135 may be a spherical or an aspheric lens surface.

In one example of operation, lens surface 123 collects incident rays from within FOV angle 180 and controls the initial propagation of those rays in compact lens system 110. The planar-concave shape of wafer-level lens 120 decreases the angles, relative to optical axis 194, of rays propagating through compact lens system 110 through a stop aperture (aperture stop 138, for example) toward the image plane of compact lens system 110. Wafer-level lens 120 thus helps avoiding large distortion. Lens surface 133 guides the rays through the stop aperture, and lens surface 135 serves to balance aberration and lead the rays to the image plane.

In an embodiment, lens surface 123 has a sag height 124. Sag height 124 is the projection onto optical axis 194 of the distance from (a) the location of lens surface 123 furthest from substrate 126 to (b) the location of lens surface 123 closest to substrate 126. Sag height 124 may relate to the diameter D1 of lens surface 123, such that $3.2 < D1/SAG1 < 4.2$. This condition ensures the feasibility of wafer-level manufacture of wafer-level lens 120 while also ensuring collection of rays from a relatively large FOV characterized by FOV angle 180.

Compact lens system 110 is designed to cooperate with an image sensor having a cover glass. Therefore, image sensor 150 includes a cover glass 154 bonded to active layer 152. Active layer 152 includes an array of photosensitive pixels and readout circuitry, and may include additional signal processing functionality. Image sensor 150 is, for example, a complementary-metal-oxide semiconductor (CMOS) image sensor, a charged coupled device (CCD), or another focal plane array.

In one embodiment, an additional substrate 156 is bonded to cover glass 154 to effectively thicken cover glass 154. Cover glass 154 and substrate 156 have a combined thickness 158 parallel to optical axis 194. Thickness 158 may be in the range from 0.6 to 1.0 mm. For comparison, a typical cover glass thickness is about 0.4 mm. The higher value of thickness 158 may help achieve the imaging quality and FOV angle 180 within a compact package defined by TTL 195 and maximum transverse extent 192. Optionally, compact lens system 110 includes substrate 156. Substrate 156 is glass, for example, or another light transmitting material. In an alternate embodiment, image sensor 150 is configured with a single cover glass of thickness 158.

Although shown in FIG. 1 as having side length matching IC diameter 190, the side length of image sensor 150 may be different from IC diameter 190. In one example, all of image sensor 150 is within IC diameter 190 such that the image formed on image sensor 150 by compact lens system 110 is free or at least nearly free of vignetting. In another example, at least a portion of the image circle characterized by IC diameter 190 is within image sensor 150, such that images captured by image sensor 150 exhibit some degree of vignetting.

In an embodiment, the effective focal length EFFL of compact lens system 110 relates to TTL 195 such that 4.4<TTL/EFFL<5.4. This condition helps achieve a small value of TTL 195, as discussed above.

In an embodiment, lens surface 123 has focal length F1, lens surface 133 has focal length F2, and lens surface 135 has focal length F3, such that 1.35<F2/EFFL<1.75 and −0.9<F1/F3<−0.7. These conditions help balance aberrations, such as astigmatism and distortion.

In an embodiment, the Abbe number of lens element 122 is greater than 48 while the Abbe number of lens element 132 is less than 35. These conditions cooperate to correct chromatic aberrations such as lateral color and axial color. In this embodiment, the Abbe number of lens element 134 may be different from that of lens element 132, for example greater than 48.

In certain embodiments, compact lens system 110 is configured to operate in the visible spectral range. However, compact lens system 110 may be configured to operate in a different spectral range, for example in the near-infrared spectral range, without departing from the scope hereof. Each of wafer-level lenses 120 and 130 is at least partly transmissive to light in the spectral range, in which compact lens system is configured to operate.

Figure 2:
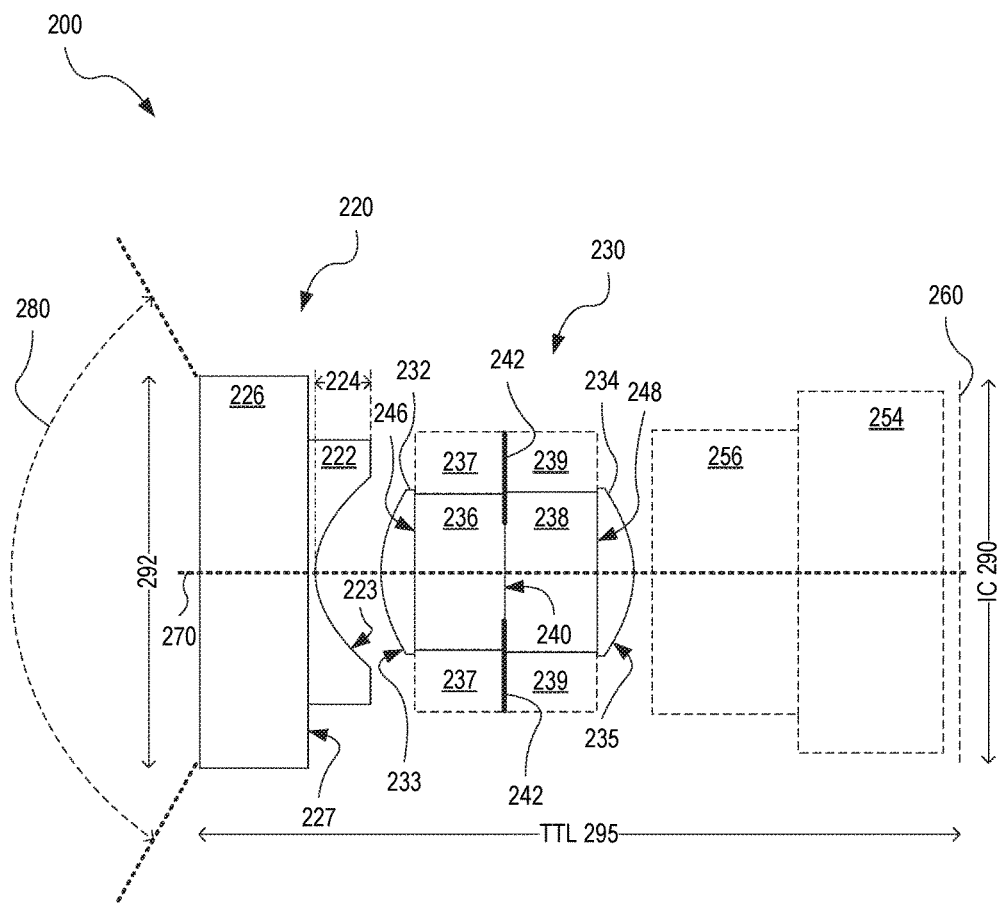
FIG. 2 illustrates one embodiment of the compact three-surface wafer-level lens system of FIG. 1.

FIG. 2 illustrates one exemplary compact, three-surface wafer-level lens system 200. Compact lens system 200 includes a one-sided wafer-level lens 220 and a two-sided wafer-level lens 230, optically coupled in series. Compact lens system 200 illustrates, by non-limiting example, the beneficial concepts discussed in connection with FIG. 1. While particular values of parameters for compact lens system 200 are disclosed, actual values may deviate from the disclosed values. A disclosed parameter value is a particular example of a range of values and may be extended to such a range of values. Compact lens system 200 is an embodiment of compact lens system 110. Wafer-level lenses 220 and 230 are embodiments of wafer-level lenses 120 and 130, respectively.

Compact lens system 200 is configured to image a scene onto an image plane 260 with a cover glass placed between compact lens system 200 and image plane 260. This cover glass is, for example, made of glass, plastic, or a combination thereof. In one embodiment, as shown in FIG. 2, this cover glass includes a cover glass 254 and an additional substrate 256 bonded thereto. In another embodiment, not shown in FIG. 2, a single substrate forms cover glass 254 and substrate 256. Cover glass 254 is an embodiment of cover glass 154, and substrate 256 is an embodiment of substrate 156. Compact lens system 200 has a total track length 295 and forms an image circle 290 on image plane 260. Compact lens system 200 has a FOV characterized by FOV angle 280. FIG. 2 further indicates the optical axis 270 of compact lens system 200.

Wafer-level lens 220 includes a substantially planar substrate 226 and a lens element 222 disposed on a substantially planar surface 227 of substrate 226. Surface 227 faces image plane 260. Lens element 222 has an aspheric concave lens surface 223 facing image plane 260. Substrate 226, lens element 222, and aspheric concave lens surface 223 are embodiments of substrate 126, lens element 122, and lens surface 123, respectively.

Wafer-level lens 230 includes two substantially planar substrates 236 and 238, a lens element 232, and a lens element 234. Substrates 236 and 238 are connected to each other at an interface 240. In one example, substrates 236 and 238 are bonded to each other. Lens element 232 is disposed on a substantially planar surface 246 of substrate 236. Surface 246 faces away from image plane 260. Lens element 232 includes an aspheric convex lens surface 233 facing away from image plane 260. Lens element 234 is disposed on a substantially planar surface 248 of substrate 238. Surface 248 faces away from image plane 260. Lens element 234 includes an aspheric convex lens surface 235 facing away from image plane 260. Wafer-level lens 230 includes a aperture stop 242 located at interface 240. Aperture stop 242 is, for example, an opaque coating. Lens elements 232 and 234 are embodiments of lens elements 132 and 134, respectively. Aspheric convex lens surfaces 233 and 235 are embodiments of lens surfaces 133 and 135, respectively. Substrates 236 and 238 together form an embodiment of substrate 136, and aperture stop 242 is an embodiment of aperture stop 138.

The use of two substrates (i.e., substrates 236 and 238) facilitates placement of aperture stop 242 between lens elements 232 and 234 and at a distance from both of lens elements 232 and 234. In contrast, if only one substrate was used, aperture stop 242 (at least if aperture stop 242 is a coating) would need to be placed at an interface between this substrate and either lens element 232 or lens element 234. If only such substrate-to-lens element interfaces were available for placement of a aperture stop, the aperture stop would have to be either (a) be placed very asymmetrically and be much closer to one side of the wafer-level lens than the other side of the wafer-level lens or (b) one of the lens elements would need to be very thick to achieve a more symmetric placement of the aperture stop with the aperture stop relatively centrally located within the wafer-level lens. In compact lens system 200, this issue is overcome by using a composite substrate with two substrates, substrates 236 and 238, such that aperture stop 242 may be placed at essentially any location within this composite substrate. In compact lens system 200, aperture stop 242 is relatively symmetrically placed between the side of wafer-level lens 230 further from image plane 260 and the side of wafer-level lens 230 closer to image plane 260 to preserve the symmetry of each ray bundle respectively associated with a field location.

Each of substrates 236 and 238 may have diameter greater than that shown in FIG. 2, without departing from the scope hereof. In one such example, substrate 236 includes an additional substrate portion 237 and substrate 238 includes an additional substrate portion 239, such that the diameter of substrate 236 is greater than the diameter of lens element 232 and the diameter of substrate 238 is greater than the diameter of lens element 234.

Without departing from the scope hereof, the diameter of one or more of lens elements 222, 232, and 234 and substrate 226 may be greater than shown in FIG. 2, although the optical performance presented below assumes optically active areas as illustrated in FIG. 2.

In operation, substrate 226 receives incident rays, which are subsequently collected by lens surface 223. Lens surface 233 adjusts the propagation direction of rays collected by lens surface 223 and directs these rays through aperture stop 242. Lens surface 235 bends bundles of rays from the respective field locations to reach image plane 260. Lens surface 235 also balances aberrations introduced by optical elements of compact lens system 200 upstream of lens surface 235.

Tables 1A, 1B and 1C lists the lens data of compact lens system 200. The lens data includes values of design parameters for substrates 226, 236, and 238, lens elements 222, 232, and 234, lens surfaces 223, 233, and 235, and aperture stop 242. The lens data also includes the configuration of substrate 256, cover glass (CG) 254, and a gap between cover glass 254 and image plane (IMA) 260. FOV angle 280 is 110 degrees, and Table 1A lists an assumed object (OBJ) location and diameter according to FOV angle 280. Material properties and thicknesses of each of substrate 226, lens element 222, lens element 232, substrate 236, substrate 238, lens element 234, cover glass 254, and substrate 256 are indicated in Table 1A in the same row as the first surface of the respective element, as viewed from the object side. Material properties indicated in Table 1A are (a) the index of refraction $n_D$ at the Fraunhofer D-line $\lambda_D$=589.3, and (b) the Abbe number. The Abbe number is a measure of optical dispersion in a material and is defined as $V_d$=$(n_D-1)/(n_F-n_C)$, where $n_F$ and $n_C$ are the indices of refraction at the Fraunhofer F-line $\lambda_F$=486.1 nm and the Fraunhofer C-line $\lambda_C$=656.3 nm, respectively.

Tables 1B and 1C list the aspheric coefficients of each of lens surfaces 223, 233, and 235. For each of these aspheric lens surfaces, the surface profile can be expressed as $$Z(s) = \frac{Cs^1}{1+\sqrt{1-(1+k)C^2s^2}} + A_4s^4 + A_6s^6 + \ldots ,$$

where Z is the surface sag parallel to optical axis 270 as a function of the radial distance s from optical axis 270, C is the inverse of the radius of curvature, k is the conic constant, and $A_4, A_6, \ldots$ are the $4^{th}, 6^{th}, \ldots$ order aspheric terms.

Compact lens system 200 has a working F-number of 3.3, effective focal length EFFL of 0.451 mm, IC diameter 290 of 1.06 mm, and TTL 295 of 2.10 mm. It follows that TTL/EFFL=4.66 for compact lens system 200.

As evident from Table 1A, lens element 232 is of a material different from that of lens element 234, while lens elements 222 and 234 have the same material properties in terms of index of refraction and Abbe number. The Abbe number of lens element 232 is 31 while the Abbe number of each of lens elements 222 and 234 is 57. In one example, lens elements 222, 232, and 234 are made from a polymer such as an epoxy. In an embodiment, compact lens system 200 is composed of reflow-compatible materials, such as materials that have identical, or substantially identical, optical properties before and after being heated to 260 degrees Celsius for 10 seconds.

Compact lens system 200 has maximum transverse extent 292 which is an example of maximum transverse extent 192. Maximum transverse extent 292 is defined by the diameter of substrate 226, which is 1.09 mm. In one embodiment, substrate 226 is square in the transverse dimensions as a result of dicing wafer-level lens 220 from a wafer, such that maximum transverse extent 292 is 1.54 mm, taken along the diagonal of the square. Sag height 224 (an example of sag height 124) of lens surface 223 is about 0.15 mm, and the diameter D1 of lens surface 223 is 0.5325 mm, such that the ratio of D1 to sag height 224 is about 3.6.

Lens surface 223 has focal length F1, lens surface 233 has focal length F2, and lens surface 235 has focal length F3, such that 1.35<F2/EFFL<1.75 and −0.9<F1/F3<−0.7.

TABLE 1A

| Surface | Radius of curvature [mm] | Thickness [mm] | $n_D$ | $V_d$ | Diameter [mm] |
|---|---|---|---|---|---|
| OBJ | Infinity | 10.0000 | | | 33.7 |
| 226 | Infinity | 0.3000 | 1.517 | 63 | 1.09 |
| 222 | Infinity | 0.0200 | 1.511 | 57 | 0.7355 |
| 223 | 0.2350 | 0.1814 | | | 0.5325 |
| 232/233 | 0.3740 | 0.0928 | 1.590 | 31 | 0.4570 |

TABLE 1A-continued

| Surface | Radius of curvature [mm] | Thickness [mm] | $n_D$ | $V_d$ | Diameter [mm] |
|---|---|---|---|---|---|
| 236 | Infinity | 0.2500 | 1.517 | 63 | 0.4351 |
| 238/STO | Infinity | 0.2550 | 1.517 | 63 | 0.1920 |
| 234 | Infinity | 0.1008 | 1.511 | 57 | 0.4469 |
| 235 | −0.3227 | 0.0500 | | | 0.4667 |
| 256 | Infinity | 0.4050 | 1.517 | 63 | 0.5766 |
| CG | Infinity | 0.4000 | 1.517 | 63 | 0.7903 |
| Gap | Infinity | 0.0450 | | | 1.0060 |
| IMA 260 | Infinity | | | | 1.0600 |

TABLE 1B

| | Aspheric coefficient | | | |
|---|---|---|---|---|
| Surface | k | $A_4$ | $A_6$ | $A_8$ |
| 223 | −0.6821 | 2.9977 | −322.1547 | 7864.9826 |
| 233 | −0.5750 | 0.4280 | −183.8806 | 9016.2761 |
| 235 | −1.0648 | −2.8303 | 554.7405 | −32309.0380 |

TABLE 1C

| | Aspheric coefficient | | |
|---|---|---|---|
| Surface | $A_{10}$ | $A_{12}$ | $A_{14}$ |
| 223 | −96105.4530 | 434407.3700 | 0.0000 |
| 233 | −193405.0000 | 1443867.6000 | 0.0000 |
| 235 | 878282.3200 | −11133684.0000 | 53006285.0000 |

FIGS. 3A, 3B, 3C, and 3D show the optical performance of compact lens system 200 (FIG. 2), as evaluated by the Zemax® Optical Design Program. FIGS. 3A, 3B, 3C, and 3D show spherical aberration, f-theta distortion, field curvature, and lateral color, respectively, of compact lens system 200, assuming location of object (OBJ) and image plane (IMA) 260 as indicated in Table 1A. As demonstrated by FIGS. 3A, 3B, 3C, and 3D, compact lens system 200 produces an image on image plane 260 of high optical quality.

Figure 3A:
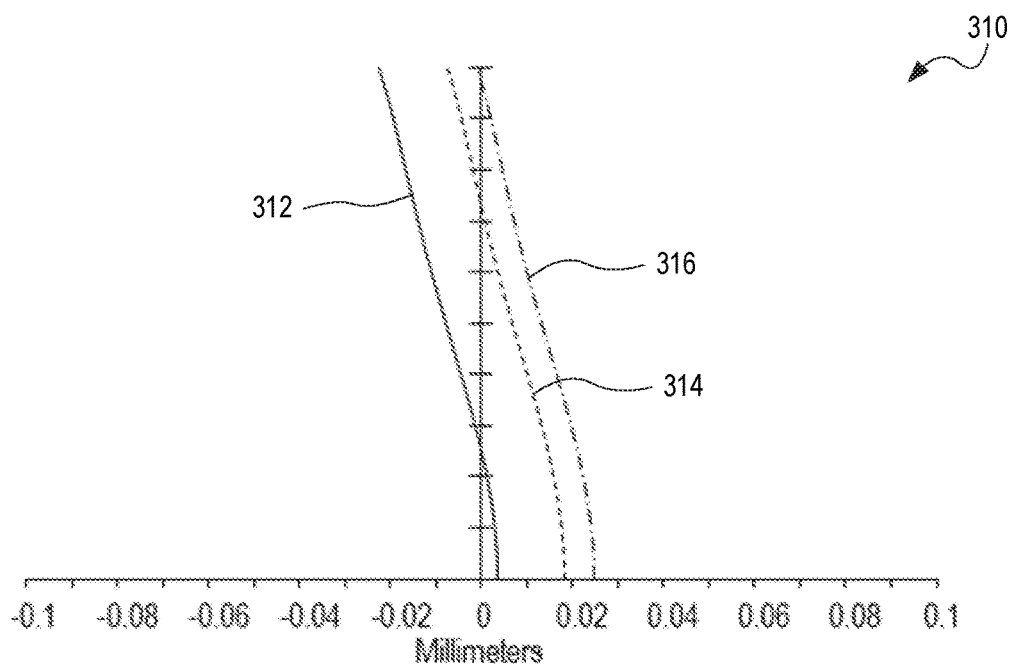
FIG. 3A is a plot of the longitudinal spherical aberration of the compact three-surface wafer-level lens system of FIG. 2.

FIG. 3A is a plot 310 of the longitudinal spherical aberration of compact lens system 200. FIG. 3A shows the longitudinal spherical aberration in millimeters, displayed on the horizontal axis, as a function of entrance pupil height, displayed on the vertical axis. The vertical axis extends from optical axis 270 to the most extreme radial distance from optical axis 270 associated with FOV angle 280. The maximum entrance pupil radius is $r_p$=0.0691 mm. Longitudinal spherical aberration curves 312 (solid line), 314 (dashed line), and 316 (dash-dot line) are computed at 486 nm, 588 nm, and 656 nm, respectively.

Figure 3B:
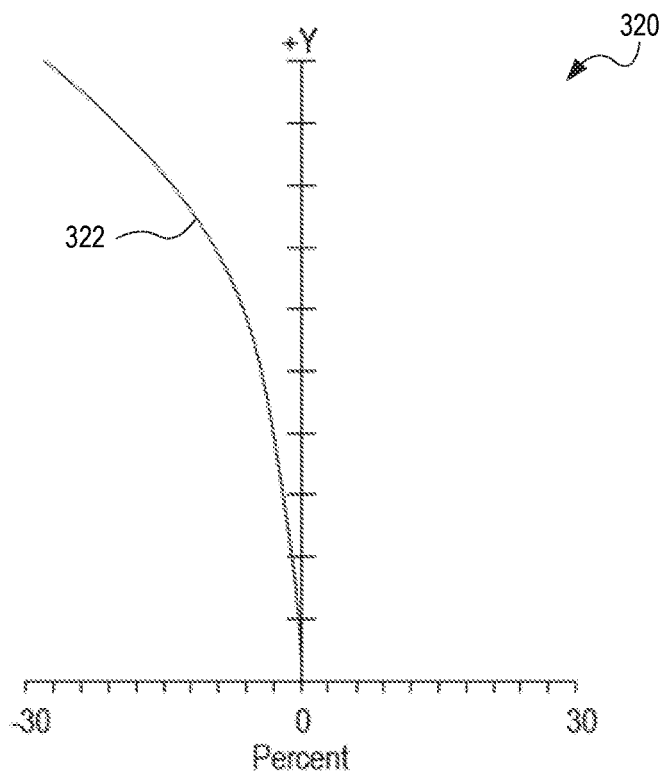
FIG. 3B is a plot of the f-theta distortion of the compact three-surface wafer-level lens system of FIG. 2.

FIG. 3B is a plot 320 of the f-theta distortion of compact lens system 200. FIG. 3B shows the f-theta distortion in percent, displayed on the horizontal axis, as a function of field angle, displayed on the vertical axis. The vertical axis extends from optical axis 270 to the most extreme location bounded by FOV angle 280. Thus, the maximum field angle plotted in FIG. 3B is $\theta_{max}$=58.549°. The distortion is the same at each of wavelengths 486 nm, 588 nm, and 656 nm, and is indicated by distortion curve 322.

Figure 3C:
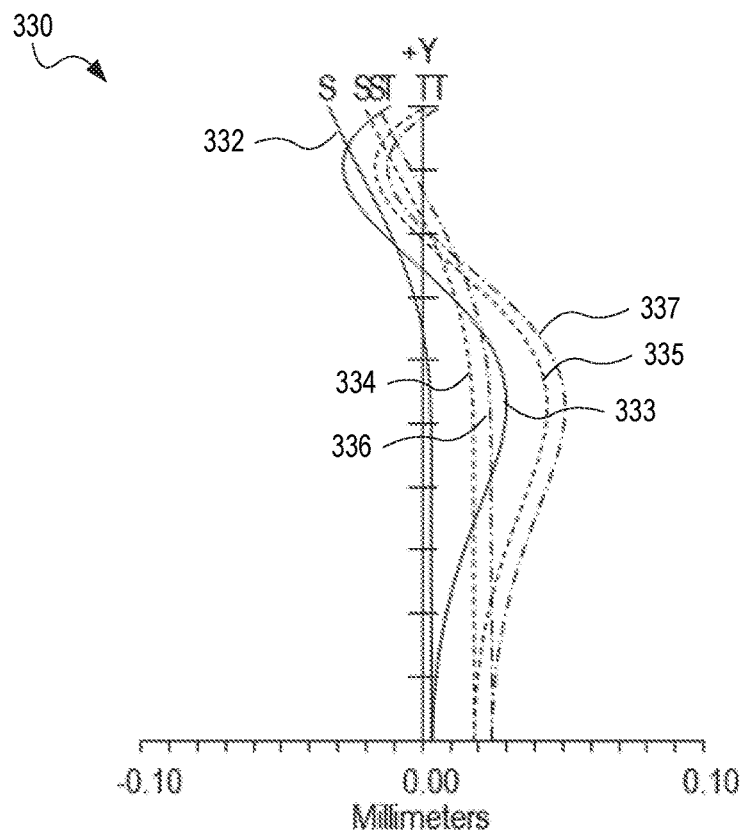
FIG. 3C is a plot of the Petzval field curvature of the compact three-surface wafer-level lens system of FIG. 2.

FIG. 3C is a plot 330 of the Petzval field curvature of compact lens system 200. The field curvature is plotted in millimeters, displayed on the horizontal axis, for field angles between zero and $\theta_{max}$=58.549°, displayed on the vertical axis. Field curvature 332 and field curvature 333 are computed at 486 nm in the sagittal (S) and tangential (T) planes, respectively. Field curvature 334 and field curvature 335 are computed at 588 nm in the sagittal (S) and tangential (T) planes, respectively. Field curvature 336 and field curvature 337 are computed at 656 nm in the sagittal (S) and tangential (T) planes, respectively.

Figure 3D:
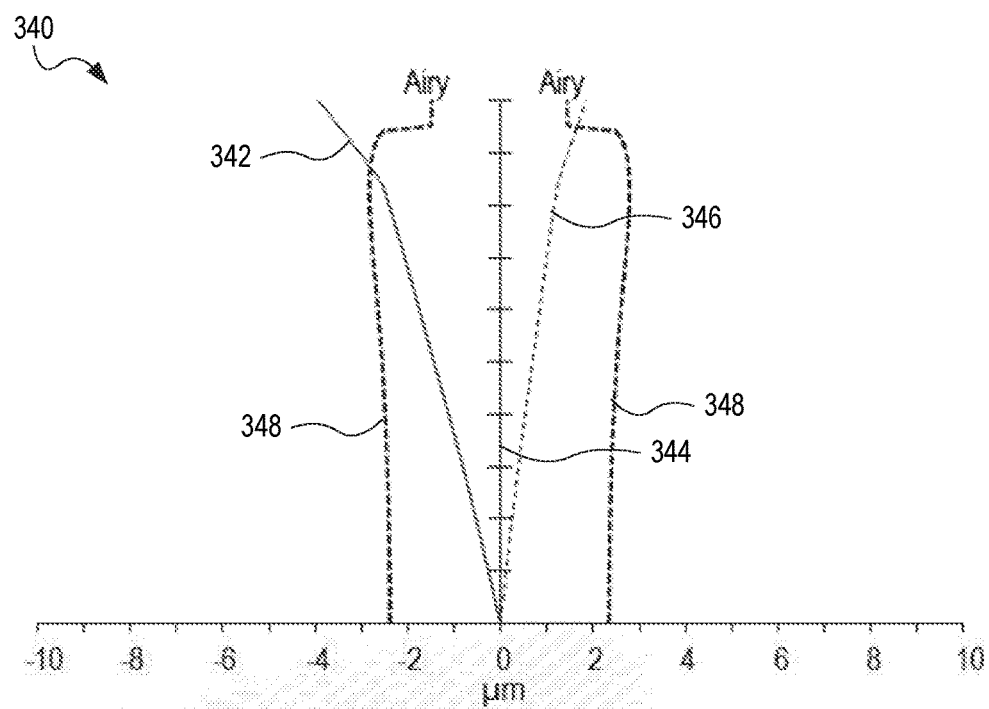
FIG. 3D is a plot of the lateral color error for the compact three-surface wafer-level lens system of FIG. 2.

FIG. 3D is a plot 340 of the lateral color error, also known as transverse chromatic aberration, for compact lens system 200. FIG. 3D shows the lateral color error in microns, displayed on the horizontal axis, as a function of field height, displayed on the vertical axis. The vertical axis extends from optical axis 270 to the most extreme radial distance from optical axis 270 associated with IC 290. Field height ranges from $h_{min}=0$ (on-axis) to $h_{max}=0.5300$ mm. Lateral color is referenced to 588 nm, such that the lateral color 344 for 588 nm is zero for all field heights. Lateral color 342 is computed at 486 nm. Lateral color 346 is computed at 656 nm.

Figure 4:
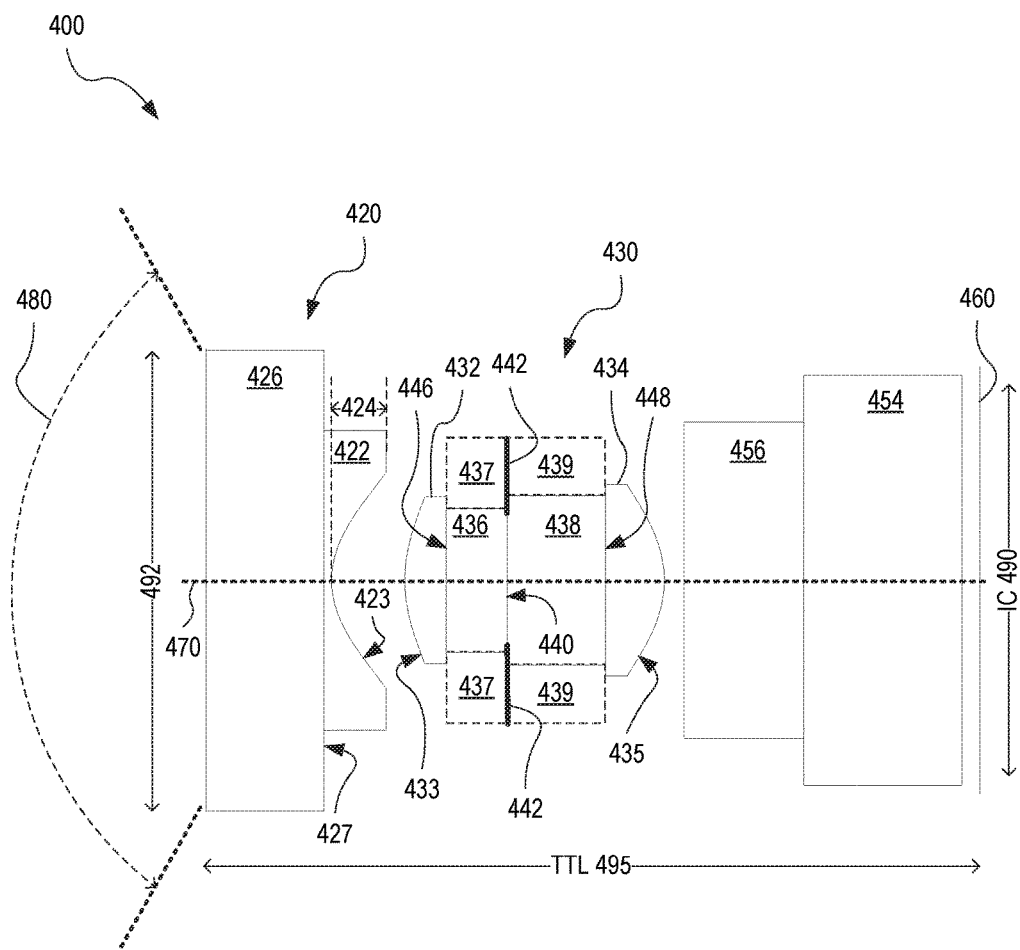
FIG. 4 illustrates another embodiment of the compact three-surface wafer-level lens system of FIG. 1.

FIG. 4 illustrates one exemplary compact, three-surface wafer-level lens system 400. Compact lens system 400 includes a one-sided wafer-level lens 420 and a two-sided wafer-level lens 430, optically coupled in series. Compact lens system 400 illustrates, by non-limiting example, the beneficial concepts discussed in connection with FIG. 1. While particular values of parameters for compact lens system 400 are disclosed, actual values may deviate from the disclosed values. A disclosed parameter value is a particular example of a range of values and may be extended to such a range of values. Compact lens system 400 is an embodiment of compact lens system 110. Wafer-level lenses 420 and 430 are embodiments of wafer-level lenses 120 and 130, respectively.

Compact lens system 400 is configured to image a scene onto an image plane 460 with a cover glass placed between compact lens system 400 and image plane 460. This cover glass is, for example, made of glass, plastic, or a combination thereof. In one embodiment, as shown in FIG. 4, this cover glass includes a cover glass 454 and an additional substrate 456 bonded thereto. In another embodiment, not shown in FIG. 4, a single substrate forms cover glass 454 and substrate 456. Cover glass 454 is an embodiment of cover glass 154, and substrate 456 is an embodiment of substrate 156. Compact lens system 400 has a total track length 495 and forms an image circle 490 on image plane 460. Compact lens system 400 has a FOV characterized by FOV angle 480. FIG. 4 further indicates the optical axis 470 of compact lens system 400.

Wafer-level lens 420 includes a substantially planar substrate 426 and a lens element 422 disposed on a substantially planar surface 427 of substrate 426. Surface 427 faces image plane 460. Lens element 422 has an aspheric concave lens surface 423 facing image plane 460. Substrate 426, lens element 422, and aspheric concave lens surface 423 are embodiments of substrate 126, lens element 122, and lens surface 123, respectively.

Wafer-level lens 430 includes two substantially planar substrates 436 and 438, a lens element 432, and a lens element 434. Substrates 436 and 438 are connected to each other at an interface 440. In one example, substrates 436 and 438 are bonded to each other. Lens element 432 is disposed on a substantially planar surface 446 of substrate 436. Surface 446 faces away from image plane 460. Lens element 432 includes an aspheric convex lens surface 433 facing away from image plane 460. Lens element 434 is disposed on a substantially planar surface 448 of substrate 438. Surface 448 faces away from image plane 460. Lens element 434 includes an aspheric convex lens surface 435 facing away from image plane 460. Wafer-level lens 430 includes a aperture stop 442 located at interface 440. Aperture stop 442 is, for example, an opaque coating. Lens elements 432 and 434 are embodiments of lens elements 132 and 134, respectively. Aspheric convex lens surfaces 433 and 435 are embodiments of lens surfaces 133 and 135, respectively. Substrates 436 and 438 together form an embodiment of substrate 136, and aperture stop 442 is an embodiment of aperture stop 138.

The use of two substrates (i.e., substrates 436 and 438) facilitates beneficial placement of aperture stop 442 between lens elements 432 and 434 and at a distance from both of lens elements 432 and 434, as discussed in reference to FIG. 2 for aperture stop 242 of compact lens system 200.

Each of substrates 436 and 438 may have diameter greater than that shown in FIG. 4, without departing from the scope hereof. In one such example, substrate 436 includes an additional substrate portion 437 and substrate 438 includes an additional substrate portion 439, such that the diameter of substrate 436 is greater than the diameter of lens element 432 and the diameter of substrate 438 is greater than the diameter of lens element 434.

Without departing from the scope hereof, the diameter of one or more of lens elements 422, 432, and 434 and substrate 426 may be greater than shown in FIG. 4, although the optical performance presented below assumes optically active areas as illustrated in FIG. 4.

In operation, substrate 426 receives incident rays, which are subsequently collected by lens surface 423. Lens surface 433 adjusts the propagation direction of rays collected by lens surface 423 and directs these rays through aperture stop 442. Lens surface 435 bends bundles of rays from the respective field locations to reach image plane 460. Lens surface 435 also balances aberrations introduced by optical elements of compact lens system 400 upstream of lens surface 435.

Tables 2A, 2B, and 2C lists the lens data of compact lens system 400. The lens data includes values of design parameters for substrates 426, 436, and 438, lens elements 422, 432, and 434, lens surfaces 423, 433, and 435, and aperture stop 442. The lens data also includes the configuration of substrate 456, cover glass (CG) 454, and a gap between cover glass 454 and image plane (IMA) 460. FOV angle 480 is 110 degrees, and Table 2A lists an assumed object (OBJ) location and diameter according to FOV angle 480. Material properties and thicknesses of each of substrate 426, lens element 422, lens element 432, substrate 436, substrate 438, lens element 434, cover glass 454, and substrate 456 are indicated in Table 2A in the same row as the first surface of the respective element, as viewed from the object side. Material properties indicated in Table 2A are the index of refraction $n_D$ at the Fraunhofer D-line and the Abbe number.

Tables 2B and 2C list the aspheric coefficients of each of lens surfaces 423, 433, and 435, according to the same coefficient definitions as used above in reference to Tables 2B and 2C.

Compact lens system 400 has a working F-number of 3.0, effective focal length EFFL of 0.377 mm, IC diameter 490 of 1.06 mm, and TTL 495 of 2.0045 mm. It follows that TTL/EFFL=5.32 for compact lens system 400.

As evident from Table 2A, lens element 432 is of a material different from that of lens element 434, while lens elements 422 and 434 have the same material properties in terms of index of refraction and Abbe number. The Abbe number of lens element 432 is 26 while the Abbe number of each of lens elements 422 and 434 is 57. In one example, lens elements 422, 432, and 434 are made from a polymer such as an epoxy. In an embodiment, compact lens system 400 is composed of reflow-compatible materials, such as materials that have identical, or substantially identical, optical properties before and after being heated to 260 degrees Celsius for 10 seconds.

Compact lens system 400 has maximum transverse extent 492 which is an example of maximum transverse extent 192. Maximum transverse extent 492 is defined by the diameter of substrate 426, which is 1.18 mm. In one embodiment, substrate 426 is square in the transverse dimensions as a result of dicing wafer-level lens 420 from a wafer, such that maximum transverse extent 492 is 1.67 mm, taken along the diagonal of the square. Sag height 424 (an example of sag height 124) of lens surface 423 is about 0.14 mm, and the diameter D1 of lens surface 423 is 0.5535 mm, such that the ratio of D1 to sag height 424 is about 4.1.

Lens surface 423 has focal length F1, lens surface 433 has focal length F2, and lens surface 435 has focal length F3, such that 1.35<F2/EFFL<1.75 and −0.9<F1/F3<−0.7.

TABLE 2A

| Surface | Radius of curvature [mm] | Thickness [mm] | $n_D$ | $V_d$ | Diameter [mm] |
|---|---|---|---|---|---|
| OBJ | Infinity | 10.0000 | | | 37.6 |
| 426 | Infinity | 0.3000 | 1.517 | 63 | 1.18 |
| 422 | Infinity | 0.0200 | 1.511 | 57 | 0.7674 |
| 423 | 0.2350 | 0.1854 | | | 0.5535 |
| 432/433 | 0.3923 | 0.1045 | 1.610 | 26 | 0.4279 |
| 436 | Infinity | 0.1550 | 1.517 | 63 | 0.3691 |
| 438/STO | Infinity | 0.2500 | 1.517 | 63 | 0.1860 |
| 434 | Infinity | 0.1491 | 1.511 | 57 | 0.4343 |
| 435 | −0.2713 | 0.0500 | | | 0.4897 |
| 456 | Infinity | 0.3050 | 1.517 | 63 | 0.6276 |
| CG | Infinity | 0.4000 | 1.517 | 63 | 0.8094 |
| Gap | Infinity | 0.0450 | | | 1.0490 |
| IMA 460 | Infinity | | | | 1.0600 |

TABLE 2B

| | Aspheric coefficient | | |
|---|---|---|---|
| Surface | k | $A_4$ | $A_6$ | $A_8$ |
| 423 | −0.9938 | 2.4879 | −295.0964 | 6995.0508 |
| 433 | −5.2191 | 6.7075 | −175.1863 | 4531.8931 |
| 435 | −12.6263 | −47.3573 | 1770.8289 | −50302.7230 |

TABLE 2C

| | Aspheric coefficient | | |
|---|---|---|---|
| Surface | $A_{10}$ | $A_{12}$ | $A_{14}$ |
| 423 | −89494.6480 | 434408.1300 | 0.0000 |
| 433 | −131437.4200 | 1443868.4000 | 0.0000 |
| 435 | 989619.0000 | −11133684.0000 | 53006285.0000 |

FIGS. 5A, 5B, 5C, and 5D show the optical performance of compact lens system 400 (FIG. 4), as evaluated by the Zemax® Optical Design Program. FIGS. 5A, 5B, 5C, and 5D show spherical aberration, f-theta distortion, field curvature, and lateral color, respectively, of compact lens system 110, assuming location of object (OBJ) and image plane (IMA) 460 as indicated in Table 2A. As demonstrated by FIGS. 5A, 5B, 5C, and 5D, compact lens system 400 produces an image on image plane 460 of high optical quality.

Figure 5A:
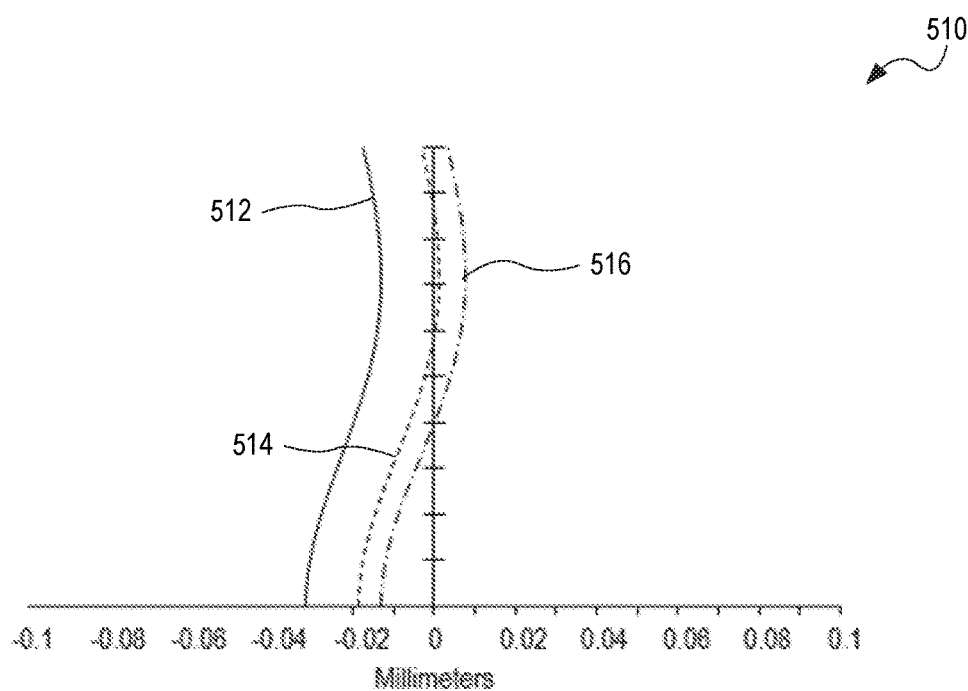
FIG. 5A is a plot of the longitudinal spherical aberration of the compact three-surface wafer-level lens system of FIG. 4.

FIG. 5A is a plot 510 of the longitudinal spherical aberration of compact lens system 400. FIG. 5A shows the longitudinal spherical aberration in millimeters, displayed on the horizontal axis, as a function of entrance pupil height, displayed on the vertical axis. The vertical axis extends from optical axis 470 to the most extreme radial distance from optical axis 470 associated with FOV angle 480. The maximum entrance pupil radius is $r_p$=0.0664 mm. Longitudinal spherical aberration curves 512 (solid line), 514 (dashed line), and 516 (dash-dot line) are computed at 486 nm, 588 nm, and 656 nm, respectively.

Figure 5B:
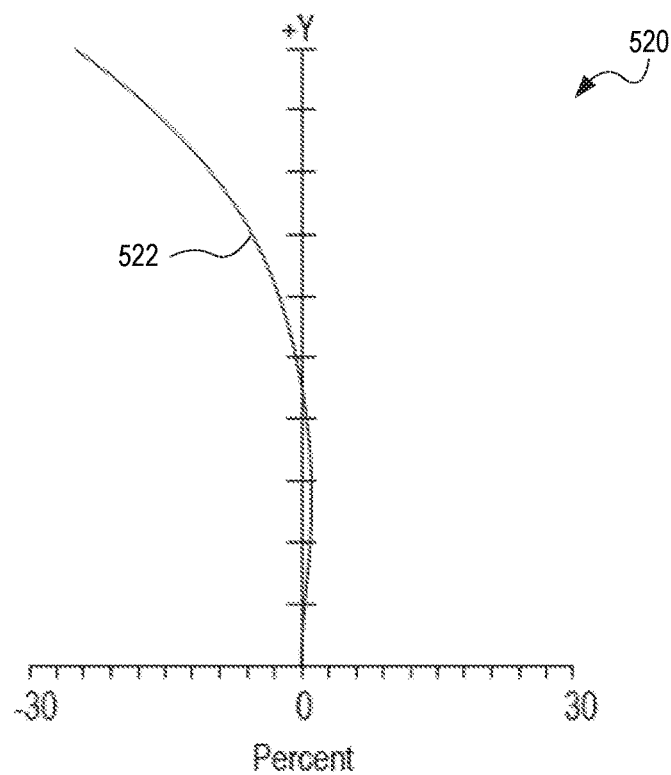
FIG. 5B is a plot of the f-theta distortion of the compact three-surface wafer-level lens system of FIG. 4.

FIG. 5B is a plot 520 of the f-theta distortion of compact lens system 400. FIG. 5B shows the f-theta distortion in percent, displayed on the horizontal axis, as a function of field angle, displayed on the vertical axis. The vertical axis extends from optical axis 470 to the most extreme location bounded by FOV angle 480. Thus, the maximum field angle plotted in FIG. 5B is $\theta_{max}$=61.293°. The distortion is the same at each of wavelengths 486 nm, 588 nm, and 656 nm, and is indicated by distortion curve 522.

Figure 5C:
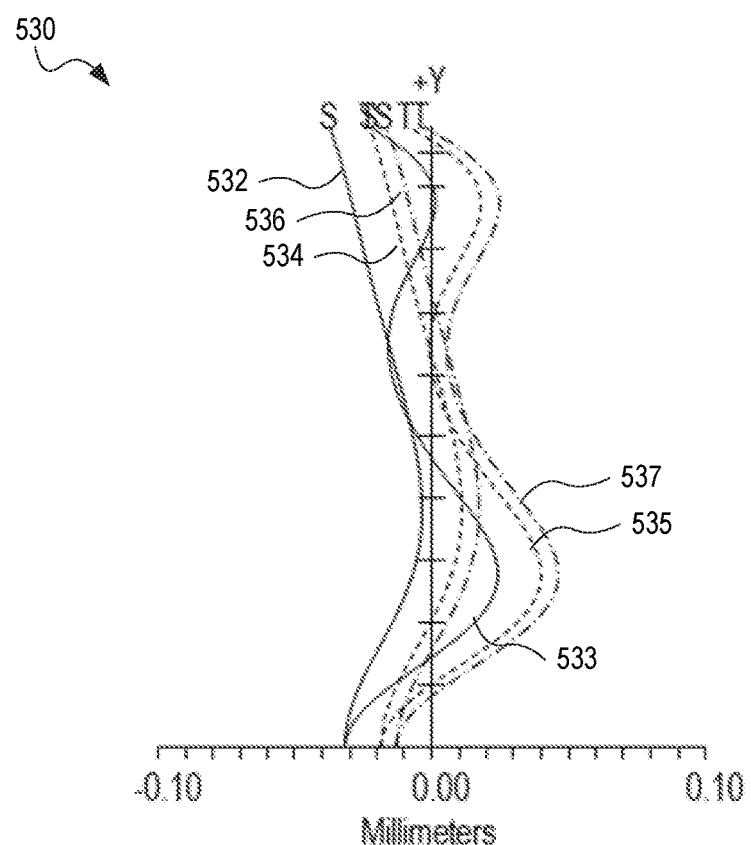
FIG. 5C is a plot of the Petzval field curvature of the compact three-surface wafer-level lens system of FIG. 4.

FIG. 5C is a plot 530 of the Petzval field curvature of compact lens system 400. The field curvature is plotted in millimeters, displayed on the horizontal axis, for field angles between zero and $\theta_{max}$=61.293°, displayed on the vertical axis. Field curvature 532 and field curvature 533 are computed at 486 nm in the sagittal (S) and tangential (T) planes, respectively. Field curvature 534 and field curvature 535 are computed at 588 nm in the sagittal (S) and tangential (T) planes, respectively. Field curvature 536 and field curvature 537 are computed at 656 nm in the sagittal (S) and tangential (T) planes, respectively.

Figure 5D:
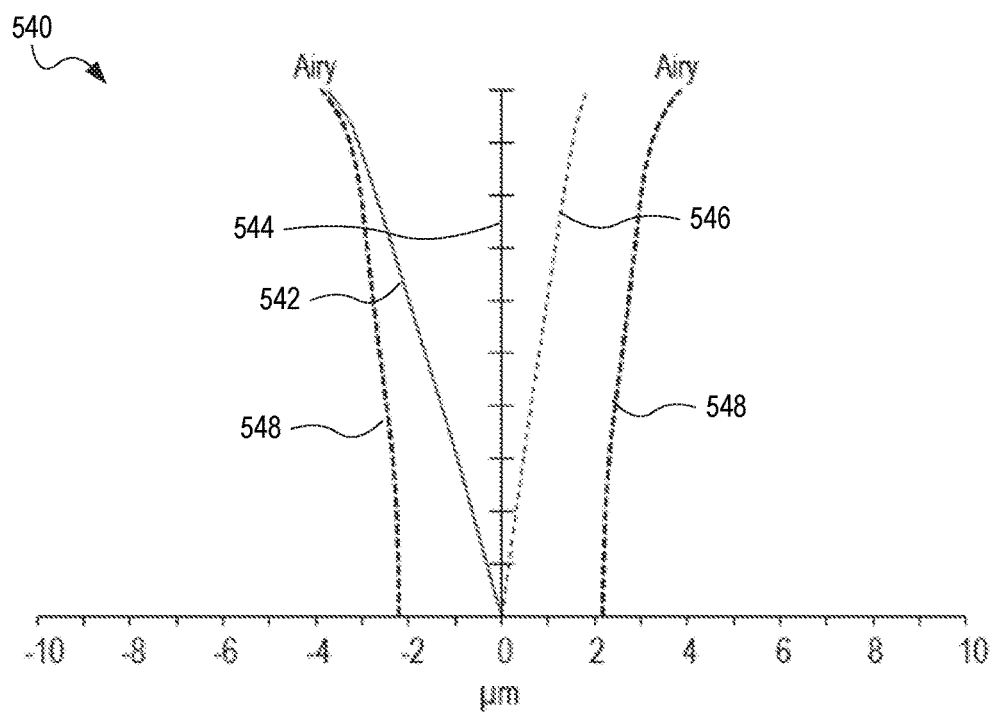
FIG. 5D is a plot of the lateral color error for the compact three-surface wafer-level lens system of FIG. 4.

FIG. 5D is a plot of the lateral color error, also known as transverse chromatic aberration, for compact lens system 400. FIG. 5D shows the lateral color error in microns, displayed on the horizontal axis, as a function of field height, displayed on the vertical axis. The vertical axis extends from optical axis 470 to the most extreme radial distance from optical axis 470 associated with IC 490. Field height ranges from $h_{min}$=0 (on-axis) to $h_{max}$=0.5876 mm. Lateral color is referenced to 588 nm, such that the lateral color 544 for 588 nm is zero for all field heights. Lateral color 542 is computed at 486 nm. Lateral color 546 is computed at 656 nm.

Figure 6:
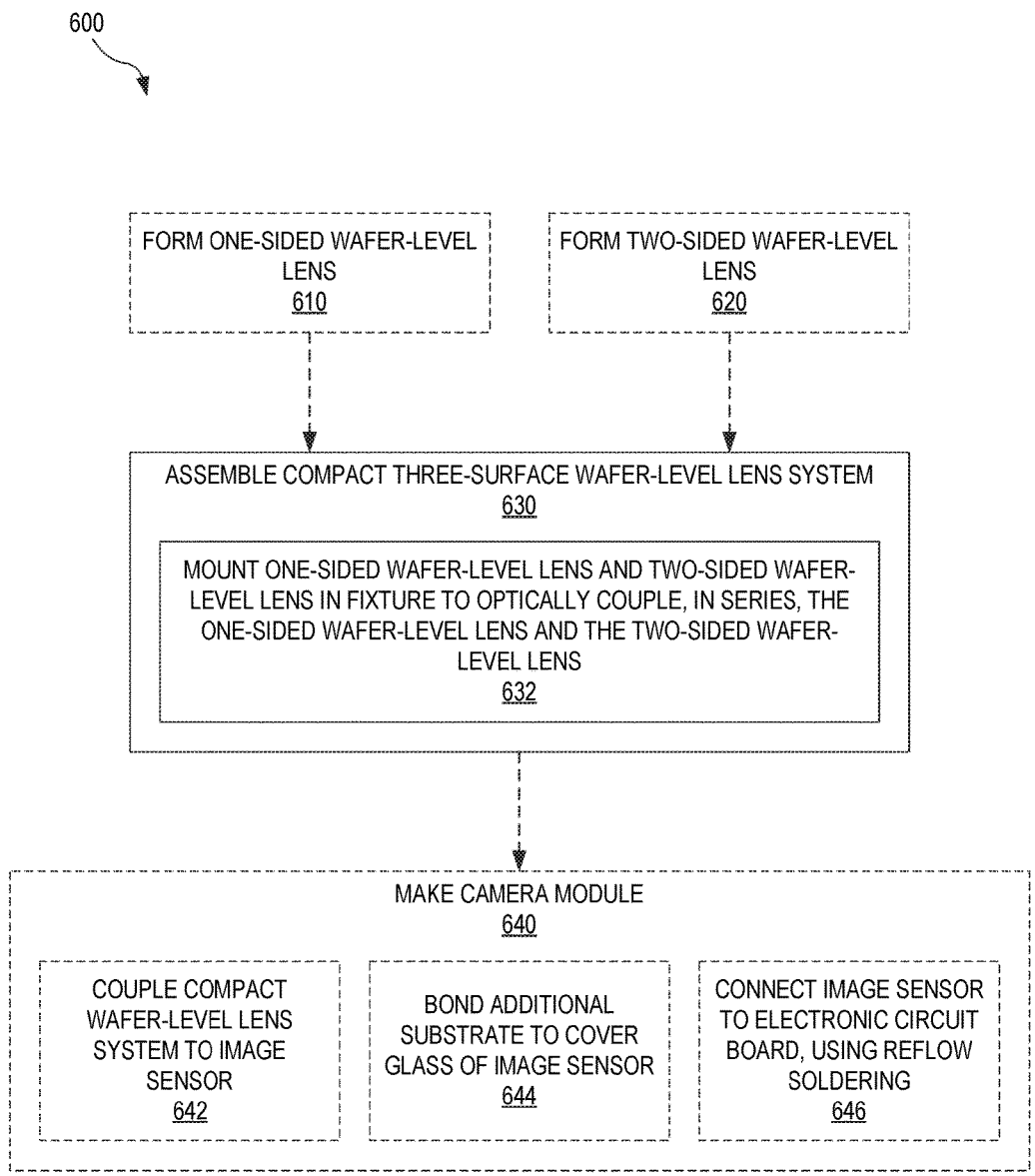
FIG. 6 illustrates a method for manufacturing a compact three-surface wafer-level lens system, according to an embodiment.

FIG. 6 illustrates one exemplary method 600 for manufacturing compact lens system 110 (FIG. 1). Method 600 may be used to form compact lens system 110 according to the lens specification of compact lens system 200 (FIG. 2) or according to the lens specification of compact lens system 400 (FIG. 4).

In a step 630, method 600 assembles compact lens system 110. Step 630 includes a step 632, wherein wafer-level lenses 120 and 130 are mounted in a fixture to optically couple wafer-level lenses 120 and 130 in series. In one example, step 632 utilizes methods known in the art to mount wafer-level lenses 120 and 130 in a fixture.

Optionally, step 630 is preceded by steps 610 and 620 of forming wafer-level lenses 120 and 130, respectively, using wafer-level lens manufacturing technology.

In an embodiment, method 600 further includes a step 640 of making camera module 100 based upon compact lens system 110, as assembled in step 630. Step 640 includes a step 642 of coupling compact lens system 110 to image sensor 150 to form camera module 100. In one example of step 642, the fixture of step 632 is mounted onto image sensor 150. In an embodiment, step 640 includes a step 644, performed prior to step 642, of bonding additional substrate 156 onto cover glass 154 of the image sensor 150. Optionally, step 640 further includes a step 646 of connecting image sensor 150 to an electronic circuit board using reflow soldering. In one example of step 646, compact lens system 110 is composed of reflow compatible materials and, after coupling lens system 110 onto image sensor 150 in step 642, the combined lens system 110/image sensor 150 assembly is electrically connected to an electronic circuit board using reflow soldering.

Figure 7:
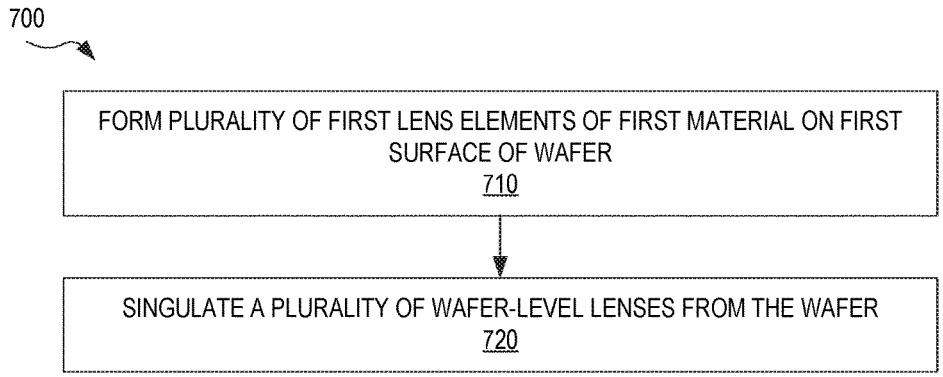
FIG. 7 illustrates a method for forming a plurality of one-sided wafer-level lenses, according to an embodiment.

FIG. 7 illustrates one exemplary method 700 for forming one-sided wafer-level lenses, such as wafer-level lens 120. Step 610 of method 600 may implement method 700.

In a step 710, a plurality of lens elements 122 are formed on a first surface of a wafer made of the material associated with substrate 126. In one embodiment of step 710, the plurality of lens elements are molded on the first surface of the wafer. For example, a resin (such as a polymer resin) is deposited onto the first surface of the wafer; a mold with a plurality of recesses, each of shape complimentary to lens surface 123, is placed on the first surface (with the resin), the resin is cured, and the mold is removed from the first surface. The resin may be an ultraviolet (UV) curable epoxy that is cured by shining UV light through the wafer to the resin on the first surface. In certain embodiments, lens elements 122 and the wafer forming substrates 126 are composed of reflow compatible materials, such as materials that have identical, or substantially identical, optical properties before and after being heated to 260 degrees Celsius for 10 seconds.

In a step 720, a plurality of wafer-level lenses 120 are singulated from the wafer. The wafer is diced, for example using methods known in the art, to form the plurality of wafer-level lenses 120.

Figure 8:
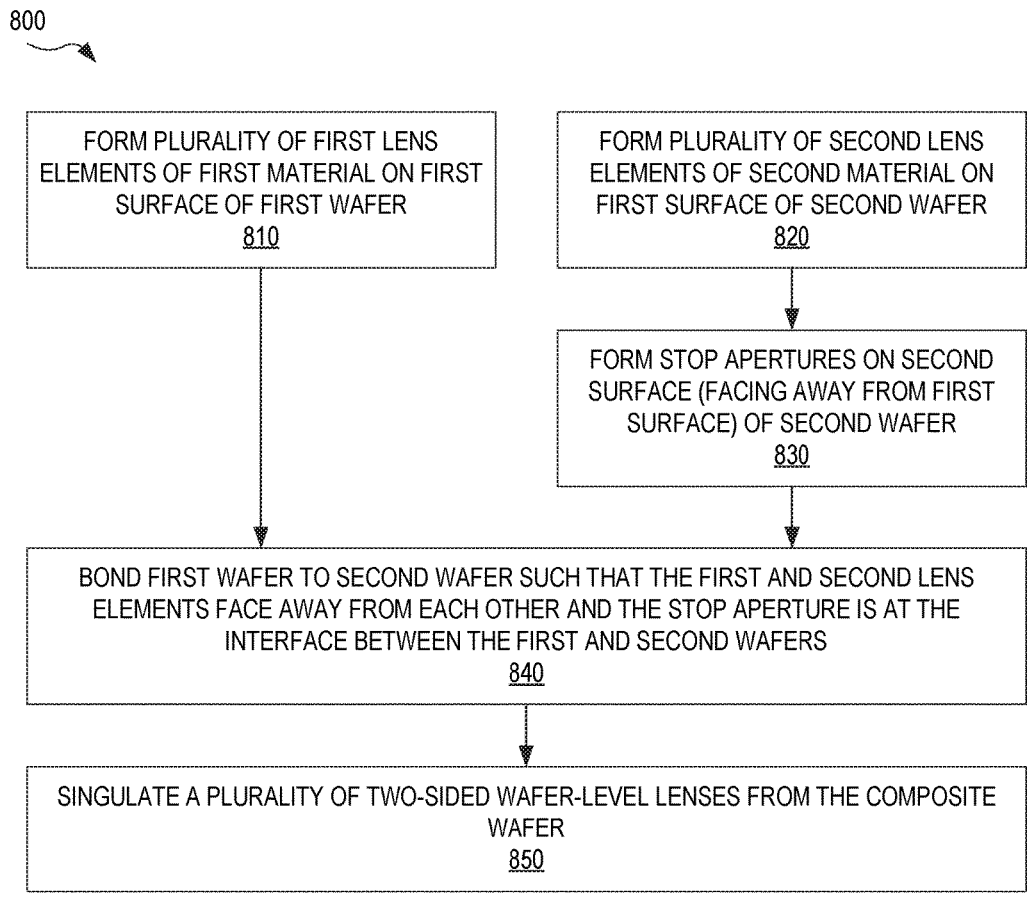
FIG. 8 illustrates a method for producing a plurality of two-sided wafer-level lenses having an internal aperture stop, according to an embodiment.

FIG. 8 illustrates one exemplary method 800 for forming two-sided wafer-level lenses each having an internal aperture stop, such as wafer-level lens 230 or 430 or an embodiment of wafer-level lens 130 having an aperture stop 138. Step 620 of method 600 may implement method 800.

In a step 810, a plurality of lens elements 132 of a first material are formed on a first surface of a wafer made of the material associated with substrate 136. In one embodiment of step 810, the plurality of lens elements 132 are molded on the first surface of the wafer. For example, a resin (such as a polymer resin) is deposited onto the first surface of the wafer; a mold with a plurality of recesses, each of shape complimentary to lens surface 133, is placed on the first surface (with the resin), the resin is cured, and the mold is removed from the first surface. The resin may be an ultraviolet (UV) curable epoxy that is cured by shining UV light through the wafer to the resin on the first surface. In one example of step 810, a plurality of lens elements 232 are formed on a wafer made of the material associated with substrate 236. In certain embodiments, lens elements 132 and the wafer forming substrates 236 are composed of reflow compatible materials, such as materials that have identical, or substantially identical, optical properties before and after being heated to 260 degrees Celsius for 10 seconds.

In a step 820, a plurality of lens elements 134 of a second material are formed on a first surface of a second wafer. Step 820 may utilize the same method as step 710, however using a mold with a plurality of recesses, each of which have shape complimentary to lens surface 135. In one example of step 820, a plurality of lens elements 234 are formed on a wafer made of the material associated with substrate 238. In one embodiment, the first material is different from the second material. In certain embodiments, lens elements 134 and the wafer forming substrates 238 are composed of reflow compatible materials, such as materials that have identical, or substantially identical, optical properties before and after being heated to 260 degrees Celsius for 10 seconds.

In a step 830, a plurality of aperture stops is formed on a second surface of the second wafer, wherein the second surface of the second wafer faces away from the first surface of the second wafer. The aperture stops are respectively aligned with lens elements 134 formed in step 820. In one example of step 830, a plurality of aperture stops 242 is formed on the wafer made of the material associated with substrate 238 and discussed in reference to step 820. In certain embodiments, the material used to form aperture stops 242 is reflow compatible, for example such that this material has identical, or substantially identical, optical properties before and after being heated to 260 degrees Celsius for 10 seconds.

In a step 840, the first wafer is bonded to the second wafer such that lens elements 132 face away from lens elements 134 and such that the aperture stop is at the interface between the first and second wafers. In one example of step 840, a wafer made of the material associated with substrate 236, and having a plurality lens elements 232, is bonded to a wafer made of the material associated with substrate 238, and having a plurality lens elements 234 and a plurality of aperture stops 242, such that aperture stops 242 are at the interface between these two wafers.

In a step 850, a plurality of wafer-level lenses 130 are singulated from the wafer formed in step 840. The wafer is diced, for example using methods known in the art, to form the plurality of wafer-level lenses 130 with aperture stops 138 internally within a two-substrate embodiment of substrate 136. In one example of step 850, the wafer produced in step 840 is singulated to form a plurality of wafer-level lenses 230.

Without departing from the scope hereof, the order of steps 820 and 830 may be reversed. Furthermore, the aperture stops formed in step 830 may instead be formed on the first wafer either before or after performing step 810, without departing from the scope hereof.

Figure 9:
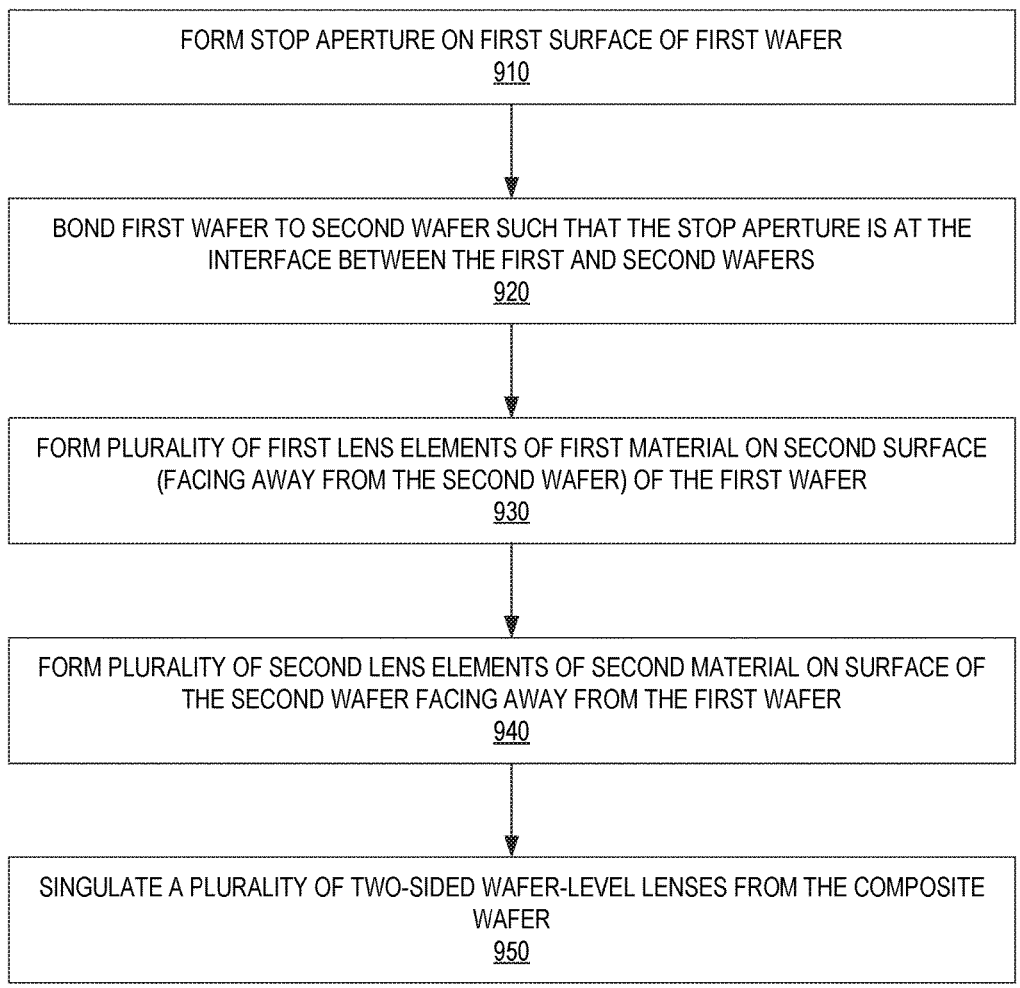
FIG. 9 illustrates another method for producing a plurality of two-sided wafer-level lenses having an internal aperture stop, according to an embodiment.

FIG. 9 illustrates another exemplary method 900 for forming two-sided wafer-level lenses each having an internal aperture stop, such as wafer-level lens 230 or 430 or an embodiment of wafer-level lens 130 having a aperture stop 138. Step 620 of method 600 may implement method 900. Method 900 is similar to method 800 but the order of operations in method 900 is rearranged, as compared to that of method 800, such that the two substrates are bonded together prior to forming the lens elements. Method 900 may utilize the same materials as discussed above for method 800.

In a step 910, a plurality of aperture stops is formed on a first surface of a first wafer, for example by applying an opaque coating to portions of the first surface. In one example of step 910, a plurality of aperture stops 242 are coated onto a wafer made of the material associated with substrate 236.

In a step 920, the first wafer is bonded to a second wafer such that the aperture stops formed in step 910 are at the interface between the two wafers. In one example of step 920, a wafer made of the material associated with substrate 236, and having a plurality of aperture stops 242 coated onto a first surface thereof, is bonded to a wafer made of the material associated with substrate 238, such that aperture stops 242 are at the interface between the two wafers.

In a step 930, a plurality of lens elements 132 of a first material are formed on a second surface of the first wafer, wherein the second surface faces away from the second wafer. In one embodiment of step 930, the plurality of lens elements 132 are molded on the second surface of the wafer. For example, a resin (such as a polymer resin) is deposited onto the first surface of the wafer; a mold with a plurality of recesses, each of shape complimentary to lens surface 133, is placed on the second surface (with the resin), the resin is cured, and the mold is removed from the first surface. The resin may be an ultraviolet (UV) curable epoxy that is cured by shining UV light through the wafer to the resin on the first surface. In one example of step 930, a plurality of lens elements 232 are formed on a composite wafer formed in step 920.

In a step 940, a plurality of lens elements 134 of a second material are formed on a second surface of the second wafer, wherein the second surface faces away from the first wafer. Step 940 may utilize the same method as step 930, however using a mold with a plurality of recesses, each of which have shape complimentary to lens surface 135. In one example of step 940, a plurality of lens elements 234 are formed on the composite wafer of step 920, on a surface facing away from the lens elements formed in step 930.

In a step 950, a plurality of wafer-level lenses 130 are singulated from the wafer formed in step 940. The wafer is diced, for example using methods known in the art, to form the plurality of wafer-level lenses 130 with aperture stops 138 internally within a two-substrate embodiment of substrate 136. In one example of step 950, the wafer produced in step 840 is singulated to form a plurality of wafer-level lenses 230.

Without departing from the scope hereof, the order of steps 930 and 940 may be reversed.

Combinations of Features

Features described above as well as those claimed below may be combined in various ways without departing from the scope hereof. For example, it will be appreciated that aspects of one compact, three-surface wafer-level lens system, or associated method of manufacture, described herein may incorporate or swap features of another compact, three-surface wafer-level lens system, or associated method of manufacture, described herein. The following examples illustrate some possible, non-limiting combinations of embodiments described above. It should be clear that many other changes and modifications may be made to the systems herein without departing from the spirit and scope of this invention:

(A1) A compact three-surface wafer-level lens system for imaging a scene onto an image plane may include a first wafer-level lens and a second wafer-level lens disposed between the first wafer-level lens and the image plane, wherein the total track length (TTL) of the wafer-level lens system is no more than 2.2 millimeters, wherein the maximum transverse extent (in dimensions transverse to the optical axis) of the lens system and associated light propagating therethrough is no greater than 1.8 millimeters, and wherein the field of view angle of the lens system is at least 100 degrees.

(A2) In the lens system denoted as (A1), the first wafer-level lens may include (a) a first substrate having a first planar surface facing the scene and a second planar surface facing the image plane, wherein the distance from the first planar surface to the image plane defines the total track length, and (b) a first lens element formed on the second planar surface and having a first lens surface facing the image plane.

(A3) In the lens system denoted as (A2), the second wafer-level lens may include (a) a second substrate having a third planar surface facing the scene and a fourth planar surface facing the image plane, (b) a second lens element bonded to the third planar surface forming a second lens surface facing the scene, and (c) a third lens element bonded to the fourth planar surface forming a third lens surface facing the image plane.

(A4) In the lens system denoted as (A3), the first lens surface may be concave, and each of the second lens surface and the third lens surface may be convex.

(A5) In either or both of the lens systems denoted as (A3) and (A4), the second substrate may be a composite substrate including a first sub-substrate closer to the scene, a second sub-substrate closer to the image plane and bonded to the first sub-substrate, and a stop aperture at interface between the first sub-substrate and the second sub-substrate.

(A6) Any of the lens systems denoted as (A3) through (A5) may have effective focal length EFFL, and the first lens element may have focal length F1, the second lens element may have focal length F2, and the third lens element may have focal length F3, such that $1.35<F2/EFFL<1.75$ and $-0.9<F1/F3<-0.7$.

(A7) In any of the lens systems denoted as (A3) through (A6), the first lens element may have Abbe number A1 greater than 48, and the second lens element may have Abbe number A2 less than 35.

(A8) In any of the lens systems denoted as (A3) through (A7), the third lens element may have Abbe number A3 greater than 48.

(A9) Any of the lens systems denoted as (A1) through (A8) may further include a planar substrate for bonding to a cover glass of an image sensor configured to capture an image formed by the three-surface wafer-level lens system at the image plane, wherein the planar substrate has thickness that cooperates with the first wafer-level lens and the second wafer-level lens to achieve the total track length and the maximum transverse extent.

(A10) Any of the lens systems denoted as (A1) through (A9) may be composed of reflow compatible materials.

(A11) Any of the lens systems denoted as (A1) through (A9) may have effective focal length EFFL such that $4.4<TTL/EFFL<5.4$.

(B1) A compact three-surface wafer-level lens system for imaging a scene onto an image plane may include a first wafer-level lens and a second wafer-level lens disposed between the first wafer-level lens and the image plane, wherein the lens system has effective focal length EFFL and total track length (TTL) such that $4.4<TTL/EFFL<5.4$.

(B2) In the lens system denoted as (B1), the first wafer-level lens may include (a) a first substrate having a first planar surface facing the scene and a second planar surface facing the image plane, wherein the distance from the first planar surface to the image plane defines the total track length (TTL) of the lens system, and (b) a first lens element formed on the second planar surface and having a first lens surface facing the image plane.

(B3) In the lens system denoted as (B2), the second wafer-level lens may include (a) a second substrate having a third planar surface facing the scene and a fourth planar surface facing the image plane, (b) a second lens element bonded to the third planar surface forming a second lens surface facing the scene, and (c) a third lens element bonded to the fourth planar surface forming a third lens surface facing the image plane.

(B4) In the lens system denoted as (B3), the first lens surface may be concave, and each of the second lens surface and the third lens surface may be convex.

(B5) Either or both of the lens systems denoted as (B3) and (B4) may have effective focal length EFFL, and the first lens element may have focal length F1, the second lens element may have focal length F2, and the third lens element may have focal length F3, such that $1.35<F2/EFFL<1.75$ and $-0.9<F1/F3<-0.7$.

(B6) In any of the lens systems denoted as (B3) through (B5), the first lens element may have Abbe number A1 greater than 48, and the second lens element may have Abbe number A2 less than 35.

(B7) In any of the lens systems denoted as (B3) through (B6), the third lens element may have Abbe number A3 greater than 48.

(B8) Any of the lens systems denoted as (B1) through (B7) may further include a planar substrate for bonding to a cover glass of an image sensor configured to capture an image formed by the three-surface wafer-level lens system at the image plane, wherein the planar substrate has thickness that cooperates with the first wafer-level lens and the second wafer-level lens to ensure that (a) the total track length is no more than 2.2 millimeters and (b) the maximum transverse extent (in dimensions transverse to optical axis) of the lens system and associated light propagating therethrough is no greater than 1.8 millimeters.

(B9) Any of the lens systems denoted as (B1) through (B8) may be composed of reflow compatible materials.

(C1) A compact three-surface wafer-level lens system for imaging a scene onto an image plane may include (a) a first wafer-level lens including (i) a first substrate having a first planar surface facing the scene and a second planar surface facing the image plane and (ii) a first lens element formed on the second planar surface and having a concave lens surface facing the image plane, wherein the concave lens surface has diameter D1 and sag height SAG1 such that $3.2<D1/SAG1<4.2$, and (b) a second wafer-level lens, disposed between the first wafer-level lens and the image plane, including (a) a first convex lens surface facing the scene, and (b) a second convex lens surface facing the image plane.

(C2) The lens system denoted as (C1) may have field of view angle of at least 100 degrees.

(C3) In either or both of the lens systems denoted as (C1) and (C2), the first lens element may have minimum thickness less than 0.03 millimeters, and D1<0.6 millimeters.

(C4) In any of the lens systems denoted as (C1) through (C3), the first lens element may have diameter no greater than 0.8 millimeters.

(C5) In any of the lens systems denoted as (C1) through (C4), the first wafer-level lens may be composed of reflow-compatible materials.

Changes may be made in the above systems and methods without departing from the scope hereof. It should thus be noted that the matter contained in the above description and shown in the accompanying drawings should be interpreted as illustrative and not in a limiting sense. The following claims are intended to cover generic and specific features described herein, as well as all statements of the scope of the present system and method, which, as a matter of language, might be said to fall therebetween.

What is claimed is:

1. A compact three-surface wafer-level lens system for imaging a scene onto an image plane, comprising:
   a first wafer-level lens including
      a first substrate having a first planar surface facing the scene and a second planar surface facing the image plane, distance from the first planar surface to the image plane defining a total track length (TTL) of the lens system of no more than 2.2 millimeters, and
      a first lens element formed on the second planar surface and having a first lens surface facing the image plane; and
   a second wafer-level lens disposed between the first wafer-level lens and the image plane and including
      a second substrate having a third planar surface facing the scene and a fourth planar surface facing the image plane,
      a second lens element bonded to the third planar surface forming a second lens surface facing the scene, and
      a third lens element bonded to the fourth planar surface forming a third lens surface facing the image plane;
   wherein maximum transverse extent, in dimensions transverse to optical axis, of the lens system and associated light propagating therethrough is no greater than 1.8 millimeters, and field of view angle of the lens system is at least 100 degrees, and wherein the lens system has effective focal length EFFL such that $1.35<F2/EFFL<1.75$ and $-0.9<F1/F3<-0.7$, F1, F2, and F3 denoting focal lengths of the first, second, and third lens elements, respectively.

2. The lens system of claim 1, the first lens surface being concave, each of the second lens surface and the third lens surface being convex.

3. The lens system of claim 1, having effective focal length EFFL such that $4.4<TTL/EFFL<5.4$.

4. The lens system of claim 1, the second substrate being a composite substrate including:
   a first sub-substrate closer to the scene;
   a second sub-substrate closer to the image plane and bonded to the first sub-substrate; and
   a stop aperture at interface between the first sub-substrate and the second sub-substrate.

5. The lens system of claim 1, the first lens element having Abbe number A1 greater than 48, the second lens element having Abbe number A2 less than 35.

6. The lens system of claim 5, the third lens element having Abbe number A3 greater than 48.

7. The lens system of claim 1, further including a planar substrate for bonding to a cover glass of an image sensor configured to capture an image formed by the three-surface wafer-level lens system at the image plane, the planar substrate having thickness that cooperates with the first wafer-level lens and the second wafer-level lens to achieve the total track length and the maximum transverse extent.

8. The lens system of claim 1, being composed of reflow compatible materials.

9. A compact three-surface wafer-level lens system for imaging a scene onto an image plane, comprising:
   a first wafer-level lens including
      a first substrate having a first planar surface facing the scene and a second planar surface facing the image plane, distance from the first planar surface to the image plane defining a total track length (TTL) of the lens system, and
      a first lens element formed on the second planar surface and having a first lens surface facing the image plane; and
   a second wafer-level lens disposed between the first wafer-level lens and the image plane and including
      a second substrate having a third planar surface facing the scene and a fourth planar surface facing the image plane,
      a second lens element bonded to the third planar surface forming a second lens surface facing the scene, and
      a third lens element bonded to the fourth planar surface forming a third lens surface facing the image plane;

wherein the lens system has effective focal length EFFL such that 4.4<TTL/EFFL<5.4 and such that 1.35<F2/EFFL<1.75 and −0.9<F1/F3<−0.7, wherein F1, F2, and F3 denote focal lengths of the first, second, and third lens elements, respectively.

10. The lens system of claim 9, the first lens surface being concave, each of the second lens surface and the third lens surface being convex.

11. The lens system of claim 9, the first lens element having Abbe number A1 greater than 48, the second lens element having Abbe number A2 less than 35.

12. The lens system of claim 11, the third lens element having Abbe number A3 greater than 48.

13. The lens system of claim 9, further including a planar substrate for bonding to a cover glass of an image sensor configured to capture an image formed by the three-surface wafer-level lens system at the image plane, the planar substrate having thickness that cooperates with the first wafer-level lens and the second wafer-level lens to ensure that (a) the total track length is no more than 2.2 millimeters and (b) maximum transverse extent, in dimensions transverse to optical axis, of the lens system and associated light propagating therethrough is no greater than 1.8 millimeters.

14. The lens system of claim 9, being composed of reflow compatible materials.

15. A compact three-surface wafer-level lens system for imaging a scene onto an image plane, comprising:
    a first wafer-level lens including
        a first substrate having a first planar surface facing the scene and a second planar surface facing the image plane, and
        a first lens element formed on the second planar surface and having a concave lens surface facing the image plane, the concave lens surface having diameter D1 and sag height SAG1 such that 3.2<D1/SAG1<4.2; and
    a second wafer-level lens, disposed between the first wafer-level lens and the image plane, including:
        a first convex lens surface facing the scene, and
        a second convex lens surface facing the image plane;
    wherein the lens system has field of view angle of at least 100 degrees.

16. The lens system of claim 15, the first lens element having minimum thickness less than 0.03 millimeters, and D1<0.6 millimeters.

17. The lens system of claim 16, the first lens element having diameter no greater than 0.8 millimeters.

18. The lens system of claim 16, the first wafer-level lens being composed of reflow-compatible materials.

* * * * *